(12) United States Patent
Li

(10) Patent No.: US 10,441,199 B2
(45) Date of Patent: Oct. 15, 2019

(54) METHOD, APPARATUS AND SYSTEM FOR MEASURING FINGER MOISTURE

(71) Applicant: SHENZHEN GOODIX TECHNOLOGY CO., LTD., Shenzhen (CN)

(72) Inventor: Yanzhao Li, Shenzhen (CA)

(73) Assignee: SHENZHEN GOODIX TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 15/784,037

(22) Filed: Oct. 13, 2017

(65) Prior Publication Data

US 2018/0353109 A1 Dec. 13, 2018

Related U.S. Application Data

(63) Continuation of application No. PCT/CN2017/087947, filed on Jun. 12, 2017.

(51) Int. Cl.
*G06K 9/00* (2006.01)
*A61B 5/1172* (2016.01)
(Continued)

(52) U.S. Cl.
CPC .......... *A61B 5/1172* (2013.01); *A61B 5/4875* (2013.01); *G06K 9/0008* (2013.01);
(Continued)

(58) Field of Classification Search
None
See application file for complete search history.

(56) References Cited

U.S. PATENT DOCUMENTS

| 5,995,640 | A |   | 11/1999 | Bolle et al. |
| 6,134,340 | A | * | 10/2000 | Hsu ..................... G06K 9/00087 |
|   |   |   |   | 382/124 |

(Continued)

FOREIGN PATENT DOCUMENTS

| CN | 102254172 A | 11/2011 |
| CN | 102708363 A | 10/2012 |

(Continued)

OTHER PUBLICATIONS

Han, Zhi et al., "Automatic Evaluation Algorithm of Fingerprint Images Quality" Computer Engineering; vol. 33, No. 19; (Oct. 2007).

(Continued)

*Primary Examiner* — Stephen P Coleman
(74) *Attorney, Agent, or Firm* — J.C. Patents

(57) ABSTRACT

The application discloses a method, an apparatus and a system for measuring finger moisture. The method includes: obtaining a fingerprint image; obtain a signal intensity and an image background intensity according to the fingerprint image; and determining finger moisture according to the fingerprint signal intensity and the image background intensity. In the method, apparatus and system for measuring finger moisture provided by the present invention, the fingerprint image is obtained and the fingerprint signal intensity and the image background intensity are obtained based on the fingerprint image, and the finger moisture is determined by analyzing the fingerprint signal intensity and the image background intensity, thereby effectively overcoming the defects in prior art in comparing and analyzing of images, including being prone to be disturbed by undulation of the image background, noise, etc., and low accuracy, thus ensuring the accuracy and reliability of the measurement of the finger moisture.

18 Claims, 8 Drawing Sheets

(51) Int. Cl.
    *A61B 5/00*   (2006.01)
    *G06K 9/62*   (2006.01)
    *G01L 13/00*  (2006.01)
(52) U.S. Cl.
    CPC ..... *G06K 9/00013* (2013.01); *G06K 9/00087* (2013.01); *G06K 9/6215* (2013.01); *A61B 5/4266* (2013.01); *A61B 2576/00* (2013.01); *G01L 13/00* (2013.01)

(56) References Cited

U.S. PATENT DOCUMENTS

| | | | |
|---|---|---|---|
| 9,953,650 B1* | 4/2018 | Falevsky | G10L 15/22 |
| 2003/0068072 A1 | 4/2003 | Hamid | |
| 2005/0069179 A1 | 3/2005 | Hwang et al. | |
| 2012/0127296 A1 | 5/2012 | Oguchi | 348/77 |

FOREIGN PATENT DOCUMENTS

| | | | | |
|---|---|---|---|---|
| CN | 103065134 | * | 4/2013 | G06K 9/00 |
| CN | 105447437 A | | 3/2016 | |
| CN | 106228108 A | | 12/2016 | |
| CN | 106250887 A | | 12/2016 | |
| EP | 1 618 842 A1 | | 1/2006 | |

OTHER PUBLICATIONS

Liu, Chengye, "Personal Fingerprint Information Wireless Collection System Based on DSP" Dissertation for the Master Degree in Engineering of Harbin University of Science and Technology; (Mar. 2017).

The Chinese First Examination Report of corresponding China patent application No. 201780000489.4, dated Jun. 15, 2018.

The Chinese International Search Report of corresponding international PCT application No. PCT/CN2017/087945, dated Mar. 21, 2018.

The extended European Search Report of corresponding European Application No. 17780616.3-1207/3441905, dated Mar. 11, 2019.

* cited by examiner

METHOD, APPARATUS AND SYSTEM FOR MEASURING FINGER MOISTURE

CROSS-REFERENCE TO RELATED APPLICATIONS

The present application is a continuation of international application No. PCT/CN2017/087945, filed on Jun. 12, 2017, which is hereby incorporated by reference in its entirety.

TECHNICAL FIELD

The invention relates to the field of fingerprint recognition technologies, especially to a method, an apparatus and a system for measuring finger moisture.

BACKGROUND

With the continuous progress of science and technologies, the fingerprint recognition technology is becoming increasingly mature, and the applicable field thereof becoming increasingly extensive. For example, the fingerprint recognition technology may be applied to the access control system (such as punching in and out for work, or home security system), electronic terminal unlocking and the medical field, etc. In the medical field, the finger moisture can be used for representing the human health information. Therefore, measurement of the finger moisture can provide reference data for medical diagnosis.

In general, all of the conventional fingerprint collection technologies would just directly collect a user's fingerprint without taking into consideration the finger moisture, in which case the collected fingerprint image is prone to be unclear when the finger is too dry or too wet, thus the quality of the collected fingerprint image is affected. On the other hand, some of the fingerprint collection technologies would first measure the finger moisture by comparing the collected image with the predefined standard image when collecting the fingerprint, to determine whether the finger is too wet or too dry.

However, the above manner for determining whether the finger is too wet or too dry has the following disadvantages: the contrast of the collected image is prone to be disturbed by the undulation of the image background, noise, etc., resulting in that the contrast of the collected image has low accuracy and is then difficult to be used accurately in quantitative measurement of finger moisture.

SUMMARY

The present invention provides a computer storage medium, and a method, an apparatus and a system for measuring finger moisture which are used to solve the problem in the prior art that the contrast of the obtained image is prone to be disturbed by the undulation of the image background, noise, etc., resulting in that the contrast of the collected image has low accuracy and is then difficult to be used accurately in quantitative measurement of finger moisture.

A first aspect of the present invention provides a method for measuring finger moisture, including:
obtaining a fingerprint image;
obtaining a fingerprint signal intensity and an image background intensity according to the fingerprint image;
determining the finger moisture according to the fingerprint signal intensity and the image background intensity.

A second aspect of the present invention provides an apparatus for measuring finger moisture, including:
an obtaining module, configured to obtain a fingerprint image;
a processing module, configured to obtain a fingerprint signal intensity and an image background intensity according to the fingerprint image; and determine the finger moisture according to the fingerprint signal intensity and the image background intensity.

A third aspect of the present invention provides a computer storage medium, in which program instructions are stored and used for implementing a method for measuring finger moisture, including:
obtaining a fingerprint image;
obtaining a fingerprint signal intensity and an image background intensity according to the fingerprint image;
determining the finger moisture according to the fingerprint signal intensity and the image background intensity.

A fourth aspect of the present invention provides a system for measuring finger moisture, including an optical imaging collector and a processor communicatively connected to the optical imaging collector;
the optical imaging collector is configured to collect a fingerprint image and send the collected fingerprint image to the processor;
the processor is configured to obtain the fingerprint image, obtain a fingerprint signal intensity and an image background intensity according to the fingerprint image, and determine the finger moisture according to the fingerprint signal intensity and the image background intensity.

In the computer storage medium, and the method, apparatus and system for measuring finger moisture provided by the present invention, the fingerprint image is obtained and the fingerprint signal intensity and the image background intensity are further obtained based on the fingerprint image, and the finger moisture is determined by analyzing the fingerprint signal intensity and the image background intensity, thereby effectively overcoming the defects in prior art in comparing and analyzing of images, including being prone to be disturbed by undulation of the image background, noise, etc., and low accuracy, thus ensuring the accuracy and reliability of the measurement of the finger moisture. Moreover, the improvement and optimization of the fingerprint collection technology as well as the accuracy and reliability of the fingerprint collection would benefit from the accurate measurement of the finger moisture, and thus the practicability of the method is effectively improved, which can facilitate the market promotion and application.

BRIEF DESCRIPTION OF DRAWINGS

For a more clear illustration of the technical solutions of embodiments of the present invention, the following drawings which are intended to be used in the description of the embodiments are briefly described. It is apparent that the drawings in the following description are merely some embodiments of the present invention, from which those skilled in the art may obtain other drawings without creative work.

DESCRIPTION OF EMBODIMENTS

The technical solution will now be described with the accompanying drawings in embodiments of the present invention, so as to clearly illustrate the purpose, technical solution and the advantages of the present invention. It is apparent that the embodiments to be described are just part rather than all of the embodiments. All other embodiments obtained by those of ordinary skill in the art based on embodiments in the present invention without making creative work are within the scope of the present invention.

Unless otherwise defined, all technical and scientific terms used herein have the same meaning as those commonly understood by the skilled in the art to which this invention pertains. The terminology used in the specification of the present invention is for the purpose of describing particular embodiments only and is not intended to limit the invention. The term "and/or" as used herein includes any and all combinations of one or more of the associated listed items.

Hereinafter, some embodiments of the present invention will be described in detail with reference to the accompanying drawings. In the case of no conflict, the embodiments and the features thereof can be combined with each other.

Figure 1:
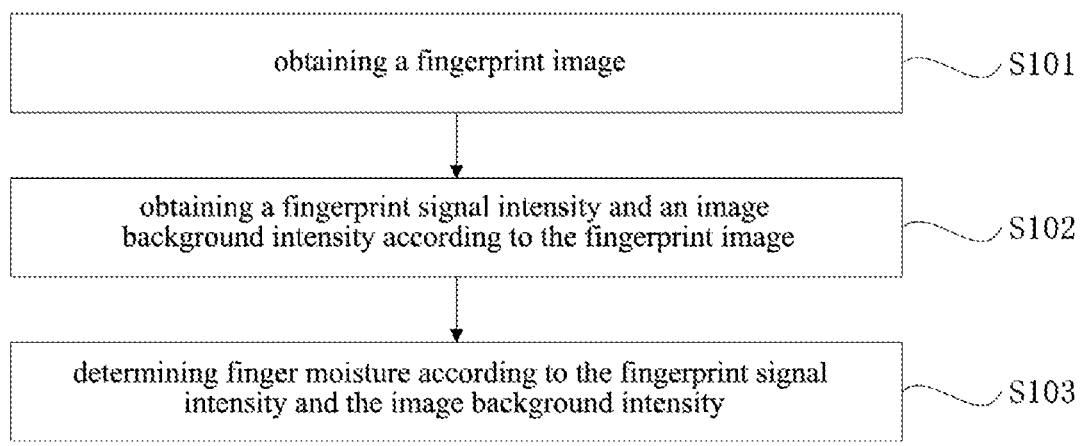
FIG. 1 is a schematic flow diagram of a method for measuring finger moisture provided by an embodiment of the present invention.

FIG. 1 is a schematic flow diagram of a method for measuring finger moisture provided by an embodiment of the present invention. With reference to FIG. 1, the embodiment provides a method for measuring finger moisture, for determining the finger moisture by analyzing a fingerprint signal of a finger. Specifically, the method includes:eb; normal S101: obtaining a fingerprint image.

The fingerprint image includes fingerprint signal information and background information, and the fingerprint image can be obtained by a fingerprint collecting device. For example, the fingerprint image is obtained by an optical fingerprint collecting device.

S102: obtaining a fingerprint signal intensity and an image background intensity according to the fingerprint image.

After obtaining the fingerprint image, optionally, correction can be performed on the fingerprint image, and then the fingerprint image or the corrected fingerprint image is analyzed to obtain the fingerprint signal intensity and the image background intensity according to the fingerprint image. The fingerprint signal intensity can be determined by obtaining the pixel values of the fingerprint signal information in the fingerprint image (for example, a ridge value and a valley value), correspondingly, the image background intensity can be determined by obtaining the pixel values of the background information in the fingerprint image. As a matter of course, those skilled in the art can also obtain the fingerprint signal intensity and the image background intensity in other ways.

S103: determining the finger moisture according to the fingerprint signal intensity and the image background intensity.

After obtaining the fingerprint signal intensity and the image background intensity, the fingerprint signal intensity and the image background intensity are analyzed to determine the finger moisture.

For example, in an optional embodiment, the fingerprint signal intensity is compared with the image background intensity, if the fingerprint signal intensity is greater than the image background intensity, it is determined that the finger moisture is relatively wet; if the fingerprint signal intensity is approximately equal to the image background intensity, it is determined that the finger moisture is relatively moderate; and if the fingerprint signal intensity is smaller than the image background intensity, it can be determined that the finger moisture is relatively dry. In an alternative embodiment, a ratio of the fingerprint signal intensity to the image background intensity can be obtained as well, and the finger moisture is determined by analyzing the ratio, for example, if the ratio is greater than a predetermined threshold or a predetermined threshold range, it is determined that the finger moisture is relatively wet; if the ratio is approximately equal to the predetermined threshold or within the predetermined threshold range, it is determined that the finger moisture is relatively moderate; and if the ratio is smaller than the predetermined threshold or the predetermined threshold range, it is determined that the finger moisture is relatively dry.

As a matter of course, those skilled in the art are also able to determine the finger moisture according to the fingerprint signal intensity and the image background intensity in other ways.

In the method for measuring finger moisture provided by this embodiment, the fingerprint image is obtained, the fingerprint signal intensity and the image background intensity are further obtained based on the fingerprint image, and the finger moisture is determined by analyzing the fingerprint signal intensity and the image background intensity, thereby effectively overcoming the defects in prior art in comparing and analyzing the collected image with the predefined standard image, including being prone to be disturbed by undulation of the image background, noise, etc., and low accuracy, thus ensuring the accuracy and reliability of the measurement of the finger moisture. Moreover, the improvement and optimization of the fingerprint collection technology as well as the accuracy and reliability of the fingerprint collection would benefit from the accurate measurement of the finger moisture. A more accurate prediction of human health information is facilitated when the method is applied in medical systems, thus the practicability of the measuring method is effectively improved, which is conductive to the market promotion and application.

Figure 2:
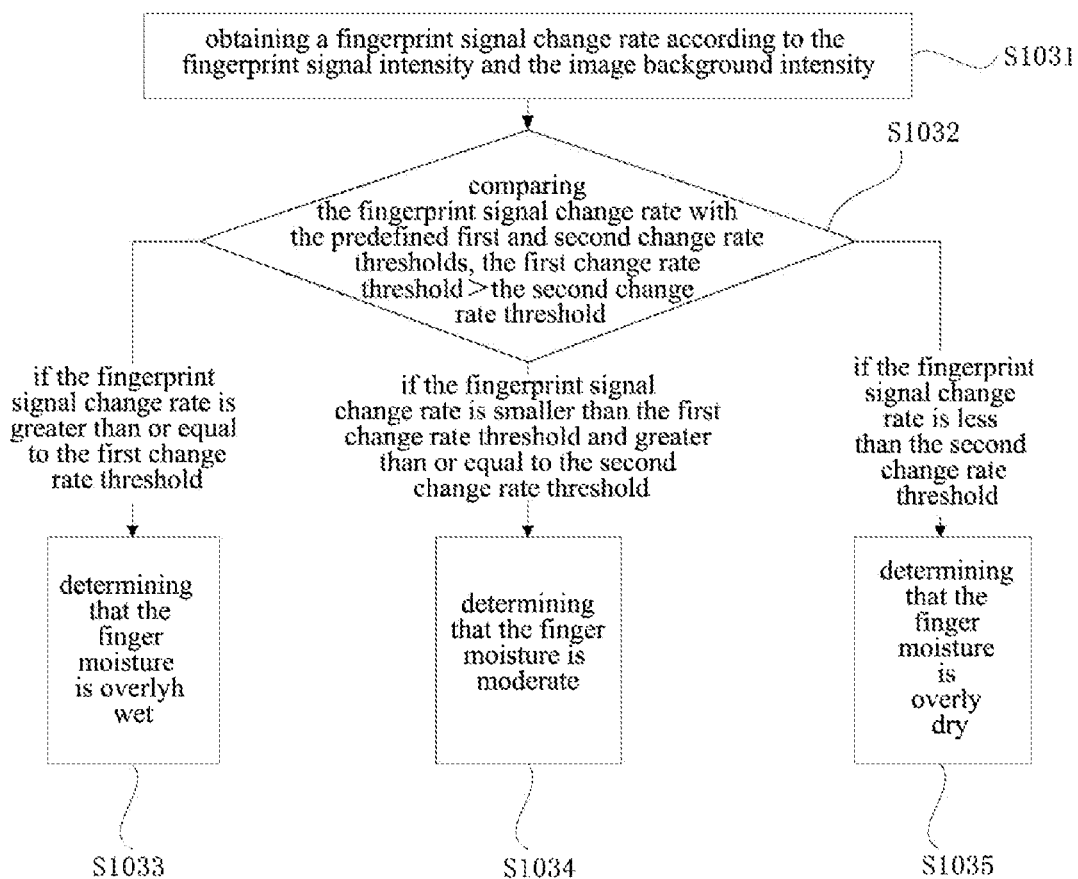
FIG. 2 is a schematic flow diagram of determining finger moisture according to a fingerprint signal intensity and an image background intensity provided by an embodiment of the present invention.

FIG. 2 is a schematic flow diagram of determining finger moisture according to a fingerprint signal intensity and an image background intensity provided by an embodiment of the present invention. On the basis of the above-mentioned embodiment, with further reference to FIGS. 1-2, the specific implementation of determining the finger moisture according to the fingerprint signal intensity and the image background intensity is not limited by the present embodiment and can be set by those skilled in the art in accordance with the specific design requirements. Preferably, determining the finger moisture according to the fingerprint signal intensity and the image background intensity can include the following steps S1031-S1035.

S1031: obtaining a fingerprint signal change rate according to the fingerprint signal intensity and the image background intensity.

The fingerprint signal change rate is obtained by analyzing the fingerprint signal intensity and the image background intensity, and is used to identify the degree of the difference between the fingerprint signal intensity and the image background intensity; specifically, obtaining the fingerprint signal change rate according to the fingerprint signal intensity and the image background intensity can include the following two implementations.

In a first possible implementation, a ratio of the fingerprint signal intensity to the image background intensity is determined to be the fingerprint signal change rate.

In that case, the fingerprint signal change rate=the fingerprint signal intensity/the image background intensity.

In a second possible implementation, a difference value between the fingerprint signal intensity and the image background intensity is obtained, a ratio of the difference value to the image background intensity is determined to be the fingerprint signal change rate.

In that case, the fingerprint signal change rate=(the fingerprint signal intensity−the image background intensity)/the image background intensity.

It should be noted that both of above-mentioned implementations can determine the fingerprint signal change rate, but values of the determined fingerprint signal change rates are different, therefore, different processing standards may be used in analyzing the determined fingerprint signal change rates.

S1032: comparing the fingerprint signal change rate with a predefined threshold range of change rate.

After obtaining the fingerprint signal change rate, the fingerprint signal change rate can be analyzed and compared with the predefined change rate threshold range. The change rate threshold range has an upper limit and a lower limit, and the upper limit of the change rate threshold range can be a first change rate threshold, while the lower limit of the change rate threshold range can be a second change rate threshold. Specifically, the first change rate threshold is the upper limit for the moderate finger moisture, while the second change rate threshold is the lower limit for the moderate finger moisture; the first change rate threshold is greater than the second change rate threshold.

S1033: if the fingerprint signal change rate is greater than or equal to an upper limit of the change rate threshold range (i.e. a first change rate threshold), it is determined that the finger moisture is overly wet.

When the fingerprint signal change rate is greater than or equal to the first change rate threshold, which indicates that the finger moisture reflected by the fingerprint signal change rate has exceeded the upper limit for the moderate finger moisture, then it can be determined that the finger moisture is overly wet. It can be understood that when the above-mentioned different implementations are employed to obtain the fingerprint signal change rate, the predefined change rate thresholds corresponding to the different determined fingerprint signal change rates are different as well.

S1034: if the fingerprint signal change rate is within the change rate threshold range, it is determined that the finger moisture is moderate.

When the fingerprint signal change rate is less than the first change rate threshold, it is indicated that the finger moisture reflected by the fingerprint signal change rate does not exceed the upper limit for the moderate moisture. In order to further accurately determine the finger moisture, the fingerprint signal change rate can be compared with the predefined second change rate threshold which is the lower limit for moderate finger moisture. Further, when the result of the comparison shows that the fingerprint signal change rate is greater than or equal to the second change rate threshold, it is indicated that the fingerprint signal change rate is within the change rate threshold range, and then it can be determined that the finger moisture is moderate.

S1035: if the fingerprint signal change rate is less than a lower limit of the change rate threshold range (i.e. a second change rate threshold), it is determined that the finger moisture is overly dry.

When the fingerprint signal change rate is less than the second change rate threshold, it can be determined that the finger moisture is overly dry because the second change rate threshold is the lower limit for moderate finger moisture, thus the finger moisture can be determined according to the fingerprint signal change rate effectively.

In the embodiment, the fingerprint signal change rate can be obtained in several different manners, which ensures the reliability of the obtained fingerprint signal change rate in various implementations, moreover improves the convenience and reliability for the user. Furthermore, by comparing the fingerprint signal change rate with the predefined different change rate thresholds, it is possible to accurately determine the finger moisture, and thus ensure the accuracy and reliability of the use of the method for measuring finger moisture.

Figure 3:
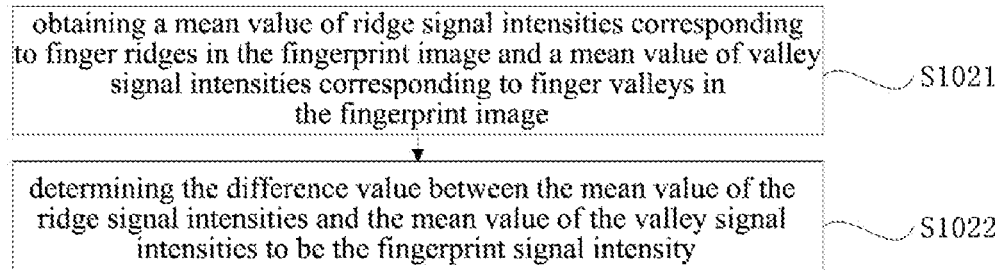
FIG. 3 is a schematic flow diagram of obtaining a fingerprint signal intensity according to a fingerprint image provided by an embodiment of the present invention.

FIG. 3 is a schematic flow diagram of obtaining a fingerprint signal intensity according to a fingerprint image provided by an embodiment of the present invention. On the basis of the above-mentioned embodiments, with a further reference to FIG. 3, the specific implementation of obtaining the fingerprint signal intensity is not limited by the present embodiment and can be set by those skilled in the art in accordance with the specific design requirements. One possible implementation for obtaining the fingerprint signal intensity according to the fingerprint image may include the following steps.

S1021: obtaining a mean value of ridge signal intensities corresponding to finger ridges in the fingerprint image and a mean value of valley signal intensities corresponding to finger valleys in the fingerprint image.

In obtaining the fingerprint image, the fingerprint image includes the finger ridges and finger valley. The ridges are streaklines having certain width and directions in the fingerprint image, which can be represented by a predetermined color e.g., black in the fingerprint image; whereas the valleys are concave parts between the streaklines, which may be also represented by a predetermined color e.g., white in the fingerprint image. Therefore, the finger ridges and finger valleys can be obtained based on the fingerprint image by image enhancement, binaryzation or other processing. Further, the ridge values of the ridges can be determined according to the pixel information at the ridge positions in the fingerprint image, and after obtaining all the ridge values, a mean value of the ridge signal intensities corresponding to the finger ridges can be obtained by summing up all the ridge values and averaging out all the ridges. Similarly, the valley values of the valleys can also be determined according to the pixel information at the valley positions in the fingerprint image, and after obtaining all the valley values, a mean value of the valley signal intensities corresponding to the finger ridges can be obtained by summing up all the valley values and averaging out all the valleys.

S1022: determining a difference value between the mean value of the ridge signal intensities and the mean value of the valley signal intensities to be the fingerprint signal intensity.

After obtaining the mean value of the ridge signal intensities and the mean value of the valley signal intensities, the mean value of the ridge signal intensities and the mean value of the valley signal intensities can be analyzed. Specifically, the difference value between the mean value of the ridge signal intensities and the mean value of the valley signal intensities is calculated, and is determined to be the fingerprint signal intensity. In other words, the mean value of the ridge signal intensities–the mean value of the valley signal intensities=the fingerprint signal intensity.

Figure 4:
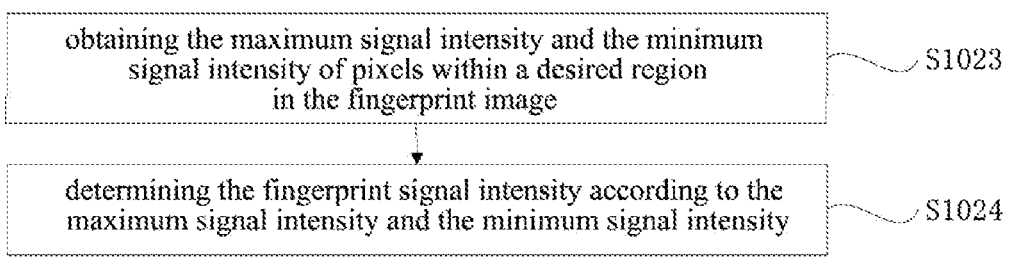
FIG. 4 is schematic flow diagram 1 of obtaining a fingerprint signal intensity according to a fingerprint image provided by another embodiment of the present invention.
Figure 5:
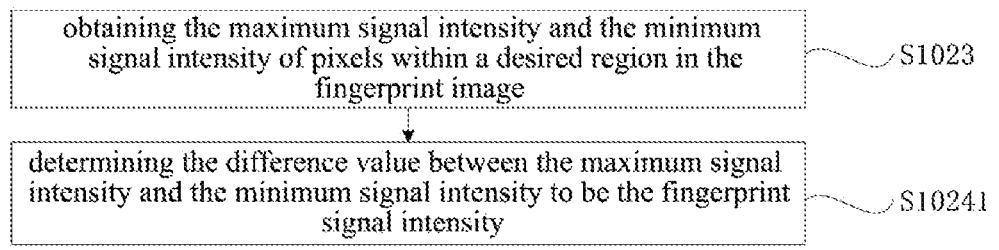
FIG. 5 is schematic flow diagram 2 of obtaining a fingerprint signal intensity according to a fingerprint image provided by another embodiment of the present invention.
Figure 6:
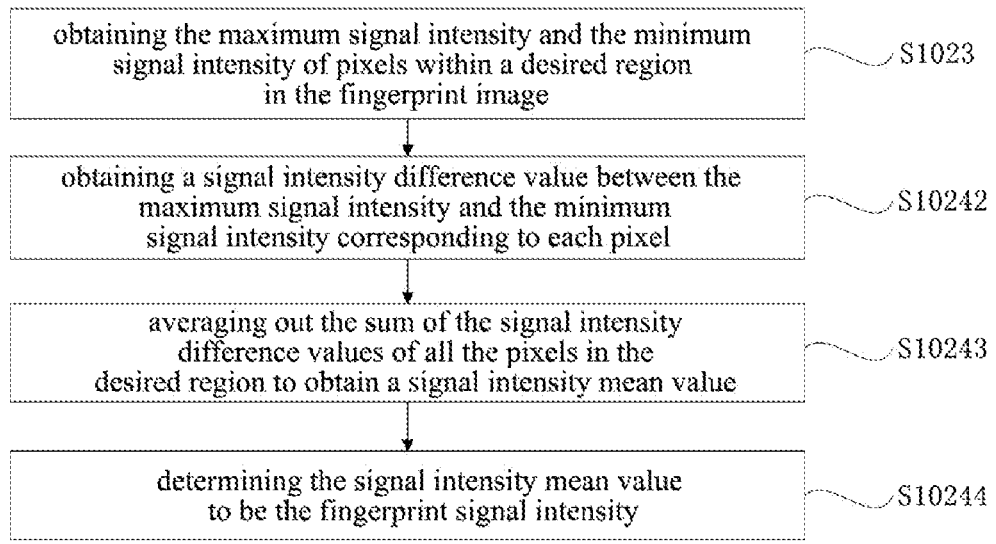
FIG. 6 is schematic flow diagram 3 of obtaining a fingerprint signal intensity according to a fingerprint image provided by another embodiment of the present invention.
Figure 7:
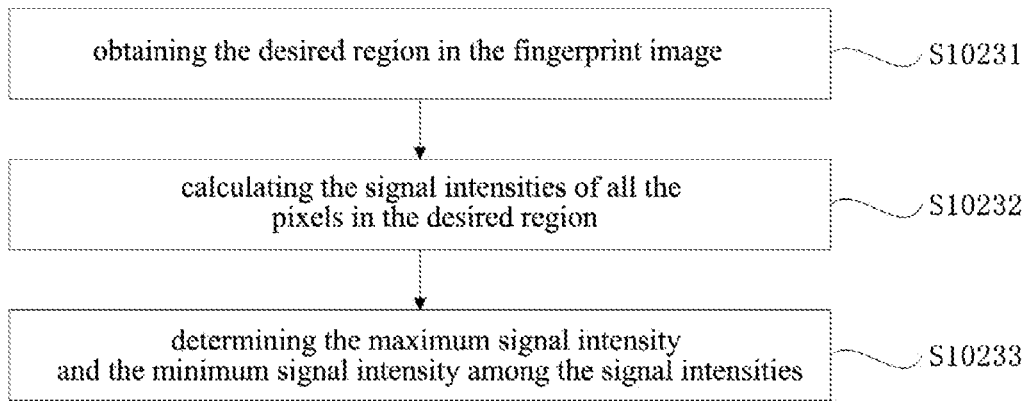
FIG. 7 is a schematic flow diagram of obtaining a maximum signal intensity and a minimum signal intensity of pixels within a desired region in a fingerprint image provided by an embodiment of the present invention.
Figure 8:
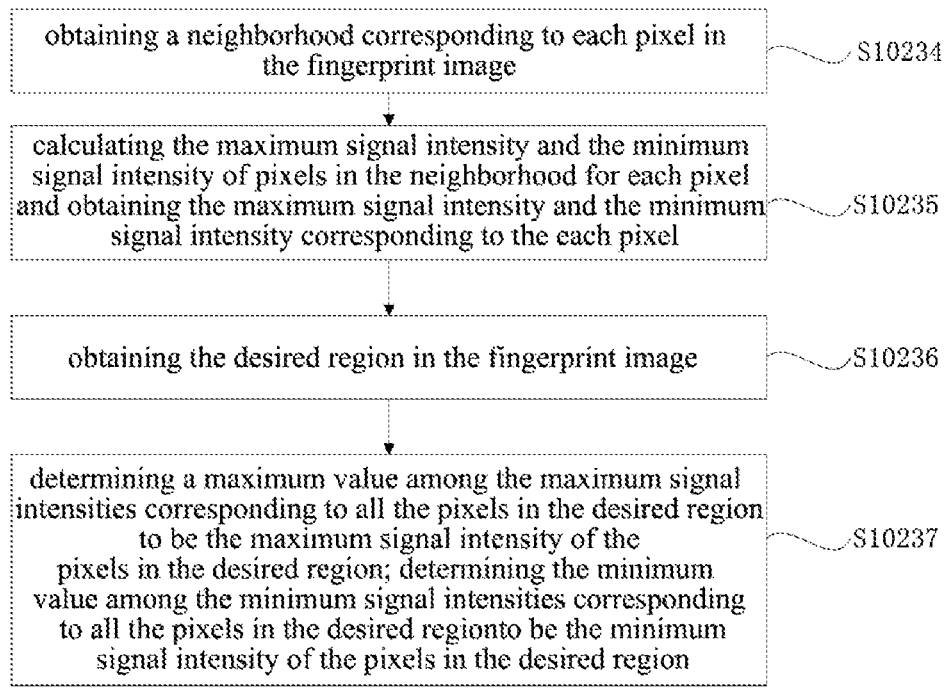
FIG. 8 is a schematic flow diagram of obtaining a maximum signal intensity and a minimum signal intensity of pixels within a desired region in a fingerprint image provided by another embodiment of the present invention.

FIG. 4 is schematic flow diagram 1 of obtaining a fingerprint signal intensity according to a fingerprint image provided by another embodiment of the present invention; FIG. 5 is schematic flow diagram 2 of obtaining a fingerprint signal intensity according to a fingerprint image provided by another embodiment of the present invention; FIG. 6 is schematic flow diagram 3 of obtaining a fingerprint signal intensity according to a fingerprint image provided by another embodiment of the present invention; FIG. 7 is a schematic flow diagram of obtaining a maximum signal intensity and a minimum signal intensity of pixels within a desired region in a fingerprint image provided by an embodiment of the present invention; FIG. 8 is a schematic flow diagram of obtaining a maximum signal intensity and a minimum signal intensity of pixels within a desired region in a fingerprint image provided by another embodiment of the present invention. Further, in addition to the above-mentioned implementations of obtaining the fingerprint signal intensity, the present embodiment provides another possible implementation with reference to FIGS. 4-8. Specifically, the fingerprint signal intensity may be obtained according to the fingerprint image in a method including the following steps S1023-S1024.

S1023: obtaining a maximum signal intensity and a minimum signal intensity of pixels within a desired region in the fingerprint image.

The desired region is an image region for the use of image processing or parameter calculation, which may be specifically a pixel region specified in the fingerprint image, and the maximum signal intensity and the minimum signal intensity of pixels within the desired region can be obtained. Specifically, with reference to FIG. 7, one possible implementation for obtaining the maximum signal intensity and the minimum signal intensity of the pixels in the desired region can include the following steps S10231-S10233.

S10231: obtaining the desired region in the fingerprint image.

The fingerprint image includes the fingerprint signal information and the background information. The above-mentioned desired region can also include the fingerprint signal information and/or the background information, therefore, users can obtain the desired region in the fingerprint image according to the specific design requirements, and a size of the desired region can be different according to different design requirements.

S10232: calculating the signal intensities of all the pixels in the desired region.

After obtaining the desired region in the fingerprint image, the signal intensities of all the pixels in the desired region can be calculated. Specifically, the signal intensity of a pixel can be calculated based on the obtained pixel value of the pixel. In general, the greater the pixel value of a pixel is, the greater the signal intensity of the pixel is; the less the pixel value of a pixel is, the less the signal intensity of the pixel is.

S10233: determining the maximum signal intensity and the minimum signal intensity.

After obtaining the signal intensities of all the pixels, all the signal intensities can be compared with each other one by one, so that the maximum signal intensity and the minimum signal intensity can be determined accurately and effectively among the signal intensities. The maximum signal intensity and the minimum signal intensity as determined are respectively the maximum signal intensity and the minimum signal intensity of the pixels in the desired region in the fingerprint image.

Furthermore, in addition to the above-mentioned manner of obtaining the maximum signal intensity and the minimum signal intensity, with reference to FIG. 8, another possible implementation for obtaining the maximum signal intensity and the minimum signal intensity of the pixels in the desired region in the fingerprint image can include the following steps S10234-S10237.

S10234: obtaining a neighborhood corresponding to each pixel in the fingerprint image.

Since the desired region is part of or all of the fingerprint image, the maximum signal intensity and the minimum signal intensity of the pixels in the desired region can also be determined by obtaining the maximum signal intensity and the minimum signal intensity of the pixels in the fingerprint image. The neighborhood corresponding to each pixel in the fingerprint image is obtained first to ensure the accuracy in obtaining the maximum signal intensity and the minimum signal intensity of the pixels in the fingerprint image; the neighborhood corresponding to a pixel refers to a surrounding region within a predefined dimension of the pixel (including the pixel); for example, a 15 mm*15 mm neighborhood of pixel A refers to the surrounding region of pixel A (including the pixel A), and the dimension of the surrounding region is 15 mm*15 mm.

S10235: for each pixel, calculating the maximum signal intensity and the minimum signal intensity of pixels in the neighborhood, and obtaining the maximum signal intensity and the minimum signal intensity corresponding to the each pixel.

After obtaining the neighborhood of each pixel, the maximum signal intensity and the minimum signal intensity in the corresponding neighborhood can be calculated for each pixel, so that the maximum signal intensity and the minimum signal intensity corresponding to each pixel are obtained.

S10236: obtaining the desired region in the fingerprint image.

The specific implementation of this step is similar to that of step S10231 described above to which details can be referred, and will not be repeated here.

S10237: determining a maximum value among the maximum signal intensities corresponding to all the pixels in the desired region to be the maximum signal intensity of pixels in the desired region; determining a minimum value among the minimum signal intensities corresponding to all the pixels in the desired region to be the minimum signal intensity of pixels in the desired region.

Since the maximum signal intensities and the minimum signal intensities corresponding to all the pixels in the fingerprint image are already known and the desired region is just part of or all of the fingerprint image, the maximum value among the maximum signal intensities corresponding to all the pixels in the desired region can be determined to be the maximum signal intensity of the pixels in the desired region, and the minimum value among the minimum signal intensities corresponding to all the pixels in the desired region can be determined to be the minimum signal intensity of the pixels in the desired region, after determining the desired region.

It will be appreciated by those skilled in the art that no matter which of the above-mentioned manners is employed to obtain the maximum signal intensity and the minimum signal intensity of the pixels in the desired region, the accuracy and reliability in obtaining the maximum signal intensity and the minimum signal intensity can be ensured.

S1024: determining the fingerprint signal intensity according to the maximum signal intensity and the minimum signal intensity.

After obtaining the maximum signal intensity and the minimum signal intensity, the maximum signal intensity and the minimum signal intensity can be analyzed, so that the fingerprint signal intensity can be determined. Specifically, the fingerprint signal intensity can be determined in the following manners.

Manner 1: step S1024 specifically includes sub-step S10241: determining a difference value between the maximum signal intensity and the minimum signal intensity to be the fingerprint signal intensity.

That is to say, the fingerprint signal intensity=the maximum signal intensity−the minimum signal intensity, therefore the fingerprint signal intensity can be obtained simply and rapidly.

Alternatively, the fingerprint signal intensity can be obtained in other manners, for example:

Manner 2: step S1024 specifically includes the following sub-steps S10242-S10244:

S10242: obtaining a signal intensity difference value between the maximum signal intensity and the minimum signal intensity corresponding to each pixel.

After obtaining the maximum signal intensity and the minimum signal intensity corresponding to each pixel, the signal intensity difference value is obtained, and the signal intensity difference value=the maximum signal intensity−the minimum signal intensity.

S10243: averaging out a sum of the signal intensity difference values of all the pixels in the desired region to obtain a signal intensity mean value.

After obtaining the signal intensity difference value of each pixel of the desired region, the sum of the signal intensity difference values of all the pixels in the desired region are averaged out, for example: if the number of pixels in the desired region is n, then the signal intensity mean value=(signal intensity difference 1+signal intensity difference 2+. . . signal intensity difference n)/n.

S10244: determining the signal intensity mean value to be the fingerprint signal intensity.

After obtaining the signal intensity mean value, the signal intensity mean value can be determined to be the fingerprint signal intensity, and the fingerprint signal intensity is obtained accurately as well.

It can be appreciated by those skilled in the art that no matter which of the above-mentioned manners is employed to obtain the fingerprint signal intensity, the fingerprint signal intensity can be obtained accurately and effectively, thus the accuracy of the method is improved.

Figure 9:
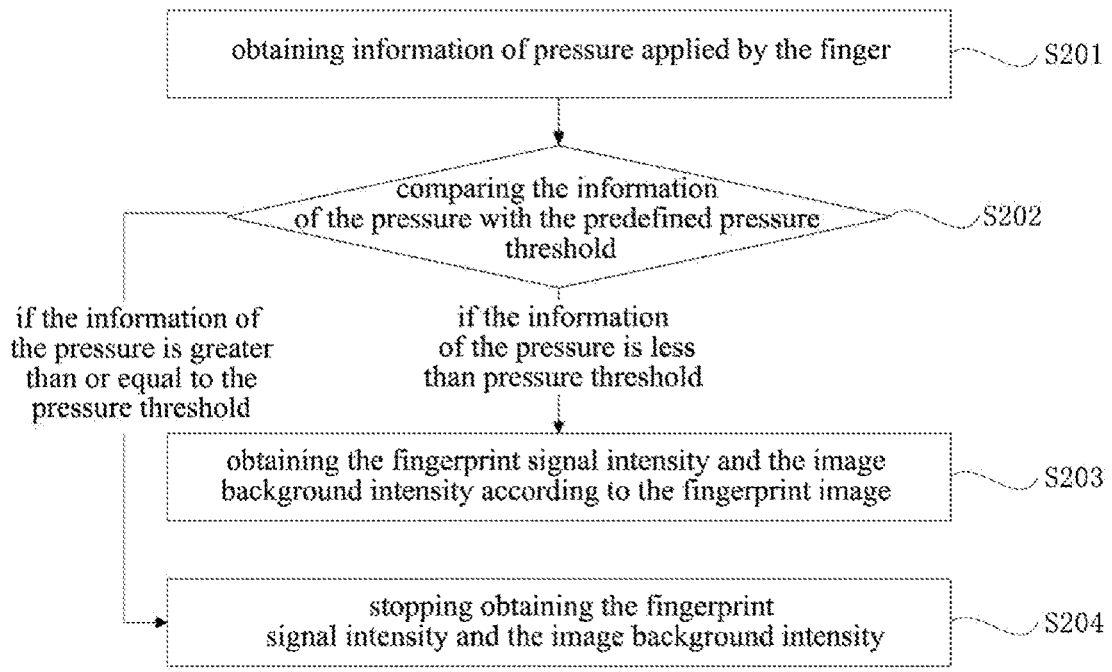
FIG. 9 is a schematic flow diagram of a method for measuring finger moisture provided by another embodiment of the present invention.

FIG. 9 is a schematic flow diagram of a method for measuring finger moisture provided by another embodiment of the present invention. On the basis of the above-mentioned embodiments and with reference to FIG. 9, in order to further ensure the accuracy and reliability of the measurement of finger moisture in specific applications, the method of this embodiment can further include:

S201: obtaining information of a pressure applied by the finger.

The information of the pressure can be obtained by detecting with a pressure sensor, and the obtained information of the pressure is used as one of the factors to decide the clarity of the fingerprint image. In general, when the fingerprint image is generated by the user's press operation, if the information of the pressure applied by the finger is relatively great, the fingerprint image is relatively clear; while if the information of the pressure applied by the finger is relatively small, the fingerprint image is relatively fuzzy, and a fuzzy fingerprint image would affect the accuracy of the measuring method. Therefore, in order to ensure the accuracy of the measuring method, a preset pressure sensor or other collecting devices can be used to obtain the information of the pressure applied by the finger in obtaining the fingerprint image. As an alternative embodiment, the information of the pressure can also be implemented through software algorithms; that is, being implemented by analyzing the clarity of the fingerprint image with algorithms It should be noted that the step S201 can be performed before, during or after the step S101 in the above-described embodiments, that is, when it is necessary to obtain the information of the pressure applied by the finger and the fingerprint image, the information of the pressure applied by the finger can be obtained first, and then the fingerprint image is obtained; or, the fingerprint image can be obtained first, then the information of the pressure applied by the finger is obtained; or, the fingerprint image can also be obtained while the information of pressure applied by the finger is obtained, and the three above-described implementations are all feasible.

S202: comparing the information of the pressure with a predefined pressure threshold.

After obtaining the information of the pressure, the information of the pressure can be analyzed. Specifically, the information of the pressure is compared with the predefined pressure threshold, which is a lower limit to decide the clarity of the fingerprint image.

S203: if the information of the pressure is greater than or equal to the pressure threshold, obtaining the fingerprint signal intensity and the image background intensity according to the fingerprint image.

If the result of analyzing and comparison is that the information of the pressure is greater than or equal to the pressure threshold, it can be determined that the currently obtained fingerprint image is relatively clear, and then the fingerprint signal intensity and the image background intensity can be obtained according to the fingerprint image.

S204: if the information of the pressure is less than the pressure threshold, stopping obtaining the fingerprint signal intensity and the image background intensity.

In analyzing and comparing the information of the pressure with the predefined pressure threshold, if the result of analyzing and comparison is that the information of the pressure is less than the pressure threshold, it can be determined that the currently obtained fingerprint image is relatively fuzzy. In order to improve the accuracy of the measuring method, the obtaining of the fingerprint signal intensity and the image background intensity is stopped. Further, in order to improve the practicability of the measuring method, a prompt message can be sent to the user, to prompt the user that the user's pressure is too small, and to apply a press operation again to generate the fingerprint image.

In this embodiment, the definition of the fingerprint image can be determined by obtaining the information of pressure applied by the finger and analyzing the information of the pressure in obtaining the fingerprint image, so as to control a further operation of the measuring method. Specifically, when the fingerprint image is relatively clear, the fingerprint signal intensity and the image background intensity can be obtained directly; when the fingerprint image is relatively fuzzy, the obtaining of the fingerprint signal intensity and the image background intensity is stopped, which further improves the accuracy of the measuring method.

Figure 10:
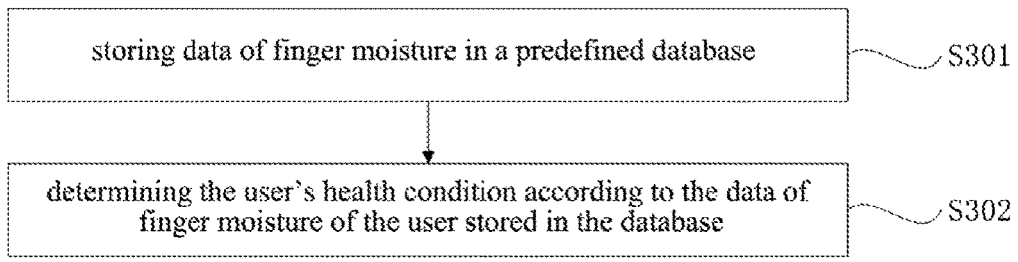
FIG. 10 is a schematic flow diagram of a method for measuring finger moisture provided by yet another embodiment of the present invention.
Figure 11:
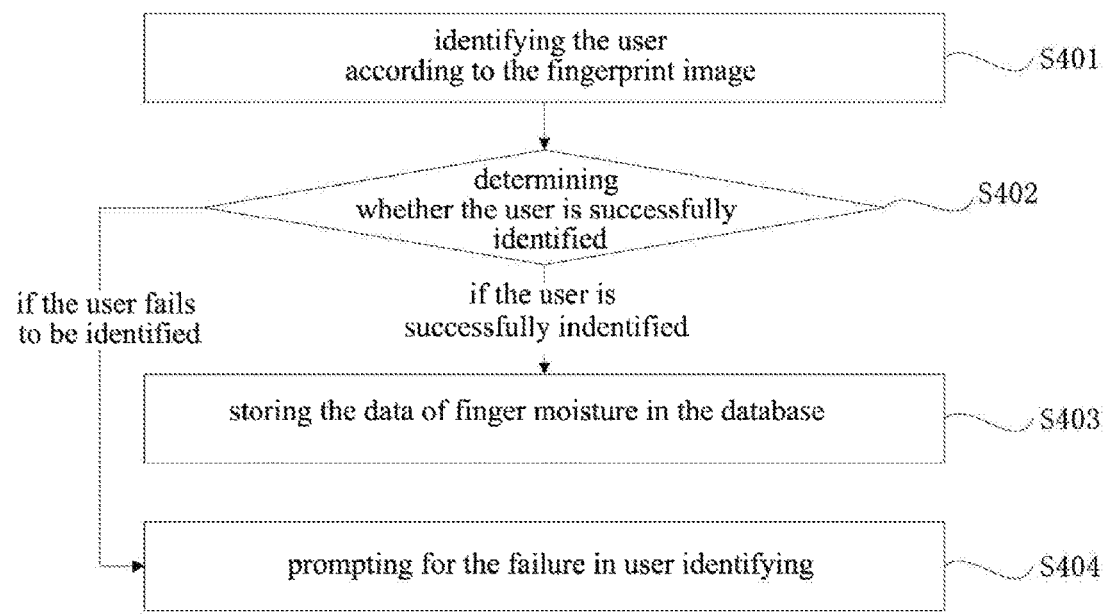
FIG. 11 is a schematic flow diagram of a method for measuring finger moisture provided by yet another embodiment of the present invention.

FIG. 10 is a schematic flow diagram of a method for measuring finger moisture provided by yet another embodiment of the present invention; FIG. 11 is a schematic flow diagram of a method for measuring finger moisture provided by yet another embodiment of the present invention. On the basis of the above-mentioned embodiments and with further reference to FIGS. 10-11, in order to further improve the practicability of the measuring method, after determining the finger moisture according to the fingerprint signal intensity and the image background intensity, the method can further includes the following steps in this embodiment.

S301: storing data of finger moisture in a predefined database.

After obtaining the data of finger moisture, since the data of finger moisture can be used to reflect human health information, in order to facilitate the reading and processing of the data of finger moisture, the data of finger moisture can be stored in a predefined database.

S302: determining a user's health condition according to the data of finger moisture of the user stored in the database.

After storing the data of finger moisture in the database, the user can call, review, read, or process the data stored in the database at any time. Specifically, the data of finger moisture of the user stored in the database can be analyzed, so that the user's health condition can be determined, and a health report of the user can be generated to facilitate the review by the user.

Further, before storing the data of finger moisture in the predefined database, the method can include the following steps.

S401: identifying the user according to fingerprint image.

In order to ensure there is one-to-one correspondence between the use and the data of finger moisture stored in the database, the user can be identified according to the fingerprint image before the data of finger moisture is stored in the predefined database. Specifically, each user has a corresponding standard fingerprint image stored in the database, therefore, the fingerprint image can be compared with standard fingerprint images stored in the database one by one, so as to identify the user's identity to ensure the safety and the reliability in storing the data of finger moisture.

S402: determining whether the user is successfully identified.

S403: if the user is successfully identified, then storing the data of finger moisture in the predefined database.

In identifying the user according to the fingerprint image, if the user is successfully identified, it is indicated that identity information corresponding to the user is pre-stored in the database, that is, the above-mentioned fingerprint image matches with a user's standard fingerprint image pre-stored in the database. Therefore, it can be determined that the user is a valid user, so that the data of finger moisture corresponding to the fingerprint image can be stored in the database, and the data of finger moisture may accordingly be stored in a storing area corresponding to data of this user.

S404: if the user fails to be identified, then prompting for the failure in user identifying.

In identifying the user according to the fingerprint image, if the user fails to be identified, it is indicated that the user's identity information is not stored in the database, that is, the above-mentioned fingerprint image does not match with any of users' standard fingerprint images pre-stored in the database. Therefore, it can be determined that the user is an invalid user, then the user can be prompted for the failure in user identifying, so as to make the user use other strategies to deal with the data of finger moisture, for example, an identity can be registered for the user first, after the registration, the data of the corresponding finger moisture of the user can be stored.

In the present embodiment, the user's identity is identified and verified, if the verification of the user's identity is passed, the data of finger moisture is stored in the corresponding storing area in the database, which facilitates the determination in the user's health condition according to the data of finger moisture of each user stored in the database, ensures the practicability of the measuring method and improves the convenience and reliability of the measuring method.

In specific applications, the method for measuring finger moisture provided by the present embodiment can include the following steps.

step A: obtaining information of a pressure applied by the finger while obtaining the fingerprint image;

step B: if the pressure is smaller than a pressure threshold, sending a prompt message to the user, where the prompt message can include content indicating that the pressure is overly small or it is necessary to increase the pressure;

step C: if the information of the pressure is greater than or equal to the pressure threshold, obtaining the fingerprint signal intensity and the image background intensity according to the fingerprint image;

step D: obtaining a fingerprint signal change rate according to the fingerprint signal intensity and the image background intensity;

step E: determining the finger moisture according to fingerprint signal change rate; specifically, if the fingerprint signal change rate is greater than or equal to the predefined first change rate threshold, it is determined that the finger moisture is overly wet; if the fingerprint signal change rate is less than the predefined first change rate threshold and greater than or equal to the predefined second change rate threshold, it is determined that the finger moisture is moderate; if the fingerprint signal change rate is less than the predefined second change rate threshold, it is determined that the finger moisture is overly dry, and a prompt message can be sent to the user, the prompt message can include the content indicating that the finger needs to be wetted suitably and then the collecting is to be performed again;

Step F: after obtaining the data of finger moisture, identifying the user's identity according to the fingerprint image; if the user is successfully identified, storing the data of finger moisture in the predefined database, and then performing step G; if the user fails to be identified, then prompting for the failure in the user identifying;

Step G: determining a user's health condition according to the data of finger moisture of the user stored in the database, and a user health report can be generated to facilitate review by the user.

Figure 12:
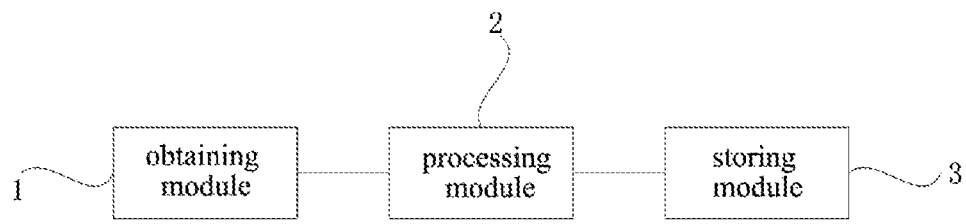
FIG. 12 is a schematic structural diagram of an apparatus for measuring finger moisture provided by an embodiment of the present invention.

FIG. 12 is a schematic structural view of an apparatus for measuring finger moisture provided by an embodiment of the present invention. With reference to FIG. 12, an apparatus for measuring finger moisture is provided by the present embodiment, and the apparatus for measuring finger moisture is used to perform the above methods for measuring the finger moisture. Specifically, the apparatus includes:

an obtaining module 1, configured to obtain a fingerprint image;

a processing module 2, configured to obtain a fingerprint signal intensity and an image background intensity according to the fingerprint image, and determine the finger moisture according to the fingerprint signal intensity and the image background intensity.

The specific principles and implementations of the apparatus for measuring finger moisture provided by the present embodiment are similar to the embodiments illustrated by FIG. 1 and will not be repeated here.

In the apparatus for measuring finger moisture provided by this embodiment, the fingerprint image is obtained by the obtaining module 1, and then the processing module 2 is used to obtain the fingerprint signal intensity and the image background intensity based on the fingerprint image, and determine the finger moisture by analyzing the fingerprint signal intensity and the image background intensity, thereby effectively overcoming the defects in prior art in comparing and analyzing of the image, including being prone to be disturbed by undulation of the image background, noise, etc., and low accuracy, thus ensuring the accuracy and reliability of the measurement of the finger moisture. Moreover, the improvement and optimization of the fingerprint collection technology as well as the accuracy and reliability of the fingerprint collection would benefit from the accurate measurement of the finger moisture. A more accurate prediction of human health information is facilitated when the apparatus is applied in medical systems, thus the practicability of the measuring apparatus is effectively improved, which is conductive to the market promotion and application.

Further, on the basis of the above-mentioned embodiments, with reference to FIG. 12, when determining the finger moisture according to the fingerprint signal intensity and the image background intensity, the processing module 2 can be configured to obtain a fingerprint signal change rate according to the fingerprint signal intensity and the image background intensity. If the fingerprint signal change rate is greater than or equal to the predefined first change rate threshold, it is determined that the finger moisture is overly wet; or, if the fingerprint signal change rate is less than the predefined first change rate threshold and greater than or equal to the predefined second change rate threshold, it is determined that the finger moisture is moderate; or, if the fingerprint signal change rate is less than the predefined second change rate threshold, it is determined that the finger moisture is overly dry.

When obtaining the fingerprint signal change rate according to the fingerprint signal intensity and the image background intensity, the processing module 2 can be configured to: determine a ratio of the fingerprint signal intensity to the image background intensity to be the fingerprint signal change rate; or, obtain a difference value between the fingerprint signal intensity and the image background intensity, and determine a ratio of the difference value to the image background intensity to be the fingerprint signal change rate.

The specific principles and implementations of the apparatus for measuring finger moisture provided by the embodiment are similar to the embodiments illustrated by FIG. 2 and will not be repeated here.

In the present embodiment, the fingerprint signal change rate can be obtained in different manners, which ensures the accuracy and the reliability of the obtained fingerprint signal change rate in various implementations, moreover improves the convenience and reliability for the user. Furthermore, by analyzing and comparing the fingerprint signal change rate with the predefined different change rate thresholds, it is possible to accurately determine the finger moisture, and thus ensure the accuracy and reliability of the use of the apparatus for measuring finger moisture.

Further, on the basis of the above-mentioned embodiments, with reference to FIG. 12, when the processing module 2 obtains the fingerprint signal intensity according to the fingerprint image, an possible implementation is that the processing module 2 can be configured to: obtain a mean value of ridge signal intensities corresponding to ridges of the finger, and a mean value of valley signal intensities corresponding to valleys of the finger in a fingerprint image; determine the difference value between the mean value of the ridge signal intensities and the mean value of the valley signal intensities to be the fingerprint signal intensity.

In another possible implementation, the processing module 2 can be configured to: obtain a maximum signal intensity and a minimum signal intensity of pixels in a desired region in the fingerprint image, and determine the fingerprint signal intensity according to the maximum signal intensity and the minimum signal intensity.

When obtaining the maximum signal intensity and the minimum signal intensity of the pixels in the desired region in the fingerprint image, as a possible implementation, the processing module 2 can be configured to: obtain the desired region in the fingerprint image, calculate signal intensities of all the pixels in the desired region; determine the maximum signal intensity and the minimum signal intensity among the signal intensities.

In another possible implementation, the processing module 2 can be configured to: obtain a neighborhood corresponding to each pixel in the fingerprint image; calculate a maximum signal intensity and a minimum signal intensity of pixels in the neighborhood for each pixel to obtain the maximum signal intensity and the minimum signal intensity corresponding to each pixel, and obtain the desired region in the fingerprint image; determine a maximum value among the maximum values corresponding to all the pixels in the desired region to be the maximum signal intensity of the pixels in the desired region; determine a minimum value among the minimum signal intensities corresponding to all the pixels in the desired region as the minimum signal intensity of the pixels in the desired region.

Moreover, when determining the fingerprint signal intensity according to the maximum signal intensity and the minimum signal intensity, the processing module 2 can be configured to: determine a difference value between the maximum signal intensity and the minimum signal intensity to be the fingerprint signal intensity, or, obtain a signal intensity difference value between the maximum signal intensity and the minimum signal intensity corresponding to each pixel; in the desired region, average out the sum of the signal intensity difference values of all the pixels in the desired region to obtain a signal intensity mean value; determine the signal intensity mean value to be the fingerprint signal intensity.

The specific principles and implementations of the apparatus for measuring finger moisture provided by the embodiment are similar to the embodiments illustrated by FIGS. 3-8 and will not be repeated here.

Further, on the basis of the above-mentioned embodiments and with reference to FIG. 12, in specific applications, in order to further ensure the accuracy and reliability of the apparatus for measuring finger moisture, the obtaining module 1 and processing module 2 in the present embodiment can be further configured to perform the following operations. Specifically, the obtaining module 1 is further configured to obtain information of a pressure applied by the finger while obtaining the fingerprint image;

the processing module 2 is further configured to: if the information of the pressure is greater or equal to the predefined pressure threshold, obtain the fingerprint signal intensity and the image background intensity according to the fingerprint image; or, if the information of the pressure is smaller than the predefined pressure threshold, stop obtaining the fingerprint signal intensity and the image background intensity.

The specific principles and implementations of the apparatus for measuring finger moisture provided by the embodiment are similar to the embodiments illustrated by FIG. 9 and will not be repeated here.

In the present embodiment, the obtaining module 1 obtains the information of pressure applied by the finger while obtaining the fingerprint image, and the processing module 2 is used to analyze the information of the pressure, so that the definition of the fingerprint image can be determined to control a further operation of the measuring apparatus. Specifically, when the fingerprint image is relatively clear, the fingerprint signal intensity and the image background intensity can be directly obtained; when the fingerprint image is relatively fuzzy, the obtaining of the fingerprint signal intensity and the image background intensity is stopped, which further improves the accuracy of the measuring apparatus.

Further, on the basis of the above-mentioned embodiments and with reference to FIG. 12, in order to further improve the practicability of the measuring apparatus, the measuring apparatus provided by the present embodiment can include:

a storing module 3, configured to store the data of finger moisture in the predefined database after determining the finger moisture according to the fingerprint signal intensity and the image background intensity;

the processing module 2 is further configured to determine a user's health condition according to the data of finger moisture of each user stored in the database.

The processing module 2 is further configured to: identify the user according to the fingerprint image before storing the data of finger moisture in the predefined database; if the user is successfully identified, then store the data of finger moisture in the predefined database; or, if the user fails to be identified, then prompt for the failure in identifying.

The specific principles and implementations of the apparatus for measuring finger moisture provided by the embodiment are similar to the embodiments illustrated by FIGS. 10-11 and will not be repeated here.

In the present embodiment, the processing module 2 identifies the user's identity, if the verification of the user's identity is passed, the storing module 3 is used to store the data of finger moisture in the corresponding storing area in the database to facilitate determining the user's health condition according to the data of finger moisture of the user stored in the database, which ensures the practicability of the measuring apparatus, and also improves the conveniences and reliability of the measuring apparatus.

Another aspect of the present application provides a computer storage medium including: a USB flash disk, mobile hard disk, read-only memory (ROM), random access memory (RAM), diskette, disk or other mediums on which program codes can be stored. In the computer storage medium there are program instructions stored which are used to implement a method for measuring finger moisture, the measuring method including:

obtaining a fingerprint image; obtaining a fingerprint signal intensity and an image background intensity according to the fingerprint image; and determining the finger moisture according to the fingerprint signal intensity and the image background intensity.

Determining the finger moisture according to the fingerprint signal intensity and the image background intensity can include: obtaining a fingerprint signal change rate according to the fingerprint signal intensity and the image background intensity; if the fingerprint signal change rate is greater than or equal to the predefined first change rate threshold, it is determined that the finger moisture is overly wet; or, if the fingerprint signal change rate is less than the predefined first change rate threshold and greater than or equal to the predefined second change rate threshold, it is determined that the finger moisture is moderate; or, if the fingerprint signal change rate is less than the predefined second change rate threshold, it is determined that the finger moisture is overly dry.

Further, obtaining the fingerprint signal change rate according to the fingerprint signal intensity and the image background intensity can include: determining a ratio of the fingerprint signal intensity to the image background intensity to be the fingerprint signal change rate; or, obtaining a difference value between the fingerprint signal intensity and the image background intensity, and determining a ratio of the difference value to the image background intensity to be the fingerprint signal change rate.

Moreover, in a possible implementation, obtaining the fingerprint signal intensity according to the fingerprint image can include: obtaining a mean value of ridge signal intensities corresponding to ridges of the finger and a mean value of valley signal intensities corresponding to valleys of the finger in the fingerprint image; determining the difference value between the mean value of the ridge signal intensities and the mean value of the valley signal intensities to be the fingerprint signal intensity.

In another possible implementation, obtaining the fingerprint signal intensity according to fingerprint image can include: obtaining a maximum signal intensity and a minimum signal intensity of pixels in a desired region in the fingerprint image, and determining the fingerprint signal intensity according to the maximum signal intensity and the minimum signal intensity.

In this case, in a possible implementation, obtaining the maximum signal intensity and the minimum signal intensity of the pixels in the desired region in the fingerprint image can include: obtaining the desired region in the fingerprint image; calculating the signal intensities of all the pixels in the desired region; determining the maximum signal intensity and the minimum signal intensity among the signal intensities.

In another possible implementation, obtaining the maximum signal intensity and the minimum signal intensity of the pixels in the desired region in the fingerprint image can include: obtaining a neighborhood corresponding to each pixel in the fingerprint image; calculating a maximum signal intensity and a minimum signal intensity of pixels in the neighborhood for each pixel, determining a maximum signal intensity and a minimum signal intensity corresponding to each pixel; obtaining the desired region in the fingerprint image; determining the maximum value among the maximum signal intensities corresponding to all the pixels in the desired region to be the maximum signal intensity of the pixels in the desired region; determining the minimum value among the minimum signal intensities corresponding to all the pixels in the desired region to be the minimum signal intensity of the pixels in the desired region.

Moreover, determining the fingerprint signal intensity according to the maximum signal intensity and the minimum signal intensity can include: determining the difference value between the maximum signal intensity and the minimum signal intensity to be the fingerprint signal intensity; or, obtaining a signal intensity difference value between the maximum signal intensity and the minimum signal intensity corresponding to each pixel; averaging out the sum of signal intensity difference values of all the pixels in the desired region to obtain a signal intensity mean value; determining the signal intensity mean value to be the fingerprint signal intensity.

Furthermore, in specific applications, in order to further ensure the accuracy and reliability of the computer storage medium, the program instructions in the computer storage medium of the embodiment can also be configured to implement the following steps. Specifically:

obtaining information of a pressure applied by the finger while obtaining the fingerprint image;

if the information of the pressure is greater than or equal to the predefined pressure threshold, obtaining the fingerprint signal intensity and the image background intensity according to the fingerprint image; or, if the information of the pressure is smaller than the predefined pressure threshold, stopping obtaining the fingerprint signal intensity and the image background intensity.

After determining the finger moisture according to the fingerprint signal intensity and the image background intensity, the method further includes: storing data of finger moisture in the predefined database; determining the user's health condition according to the data of finger moisture of each user stored in the database.

Further, before storing the data of finger moisture in the predefined database, the method can further include: identifying the user according to the fingerprint image; if the user is successfully identified, storing the data of finger moisture in the predefined database; or, if the user fails to be identified, then prompting for the failure in user identifying.

The specific principles and implementations of the computer storage medium provided by the embodiment are similar to the embodiments illustrated by FIGS. 1-11 and will not be repeated here.

In terms of the computer storage medium provided by the embodiment, there are program instructions stored therein for implementing the method for measuring finger moisture. Specifically, in the method, the fingerprint image is obtained, and then the fingerprint signal intensity and the image background intensity are further obtained based on the fingerprint image, and the finger moisture is determined by analyzing the fingerprint signal intensity and the image background intensity, thereby effectively overcoming the defects in prior art in comparing and analyzing of the image, including being prone to be disturbed by undulation of the image background, noise, etc., and low accuracy, thus ensuring the accuracy and reliability of the measurement of the finger moisture. Moreover, the improvement and optimization of the fingerprint collection technology as well as the accuracy and reliability of the fingerprint collection would benefit from the accurate measurement of the finger moisture. And a more accurate prediction of human health information is facilitated when the method is applied in medical systems, thus the practicability of the measuring apparatus is effectively improved, which is conductive to the market promotion and application.

Figure 13:
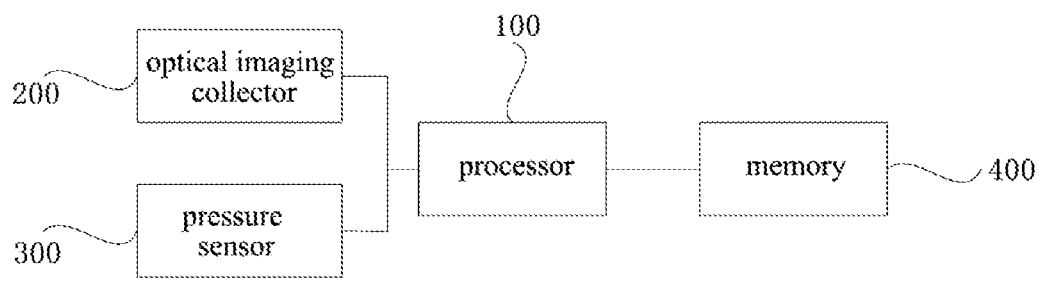
FIG. 13 is a schematic structural diagram of a system for measuring finger moisture provided by an embodiment of the present invention.

FIG. 13 is a schematic structural view of a system for measuring finger moisture provided by an embodiment of the present invention; with reference to FIG. 13, the present embodiment provides a system for measuring finger moisture, the system including: an optical imaging collector 200 and a processor 100 communicatively connected with the optical imaging collector 200;

the optical imaging collector 200 is configured to collect a fingerprint image and send the collected fingerprint image to the processor 100;

the processor 100 is configured to obtain the fingerprint image, obtain a fingerprint signal intensity and an image background intensity according to the fingerprint image, and determine the finger moisture according to the fingerprint signal intensity and the image background intensity.

It should be noted that the processor 100 in the present embodiment may only have the function of data processing, and may also have the functions of data processing and program storing; for example: the processor 100 may be a central processing unit (CPU) which has the above-mentioned data processing function, in that case, the program instructions operated by the processor 100 may be stored in a predefined memory 400 separately; or, the processor may be a micro-control unit (MCU) with an on-chip ROM, where the ROM is a read-only memory configured to store the program instructions corresponding to the above method for measuring finger moister, and the MCU can execute the instructions to implement the above-described data processing function. Therefore, an implementable structure of the system for measuring the finger moisture includes: the optical imaging collector 200, the processor 100 and the memory 400; alternatively, another implementable structure of the system for measuring the finger moisture includes: the optical imaging collector 200 and the processor 100. Moreover, the specific principles and implementations of the system for measuring the finger moisture provided by the embodiment are similar to the embodiments illustrated by FIG. 1 and will not be repeated here.

In the system for measuring finger moisture provided by this embodiment, the fingerprint image is obtained by the optical imaging collector 200, and then the processor 100 is used to obtain the fingerprint signal intensity and the image background intensity based on the fingerprint image, and determine the finger moisture by analyzing the fingerprint signal intensity and the image background intensity, thereby effectively overcoming the defects in prior art in comparing and analyzing of the image, including being prone to be disturbed by undulation of the image background, noise, etc., and low accuracy, thus ensuring the accuracy and reliability of the measurement of the finger moisture. Moreover, the improvement and optimization of the fingerprint collection technology as well as the accuracy and reliability of the fingerprint collection would benefit from the accurate measurement of the finger moisture. And a more accurate prediction of human health information is facilitated when the system is applied in medical systems, thus the practicability of the measuring system is effectively improved, which is conductive to the market promotion and application.

On the basis of the above-mentioned embodiments, with reference to FIG. 13, when the processor 100 determines the finger moisture according to the fingerprint signal intensity and the image background intensity, the processor 100 can be configured to: obtain a fingerprint signal change rate according to the fingerprint signal intensity and the image background intensity; if the fingerprint signal change rate is greater than or equal to the predefined first change rate threshold, it is determined that the finger moisture is overly wet; or, if the fingerprint signal change rate is less than the predefined first change rate threshold and greater than or equal to the predefined second change rate threshold, it is determined that the finger moisture is moderate; or, if the fingerprint signal change rate is less than the predefined second change rate threshold, it is determined that the finger moisture is overly dry.

When the processor 100 obtains the fingerprint signal change rate according to the fingerprint signal intensity and the image background intensity, the processor 100 can be configured to: determine a ratio of the fingerprint signal intensity to the image background intensity to be the fingerprint signal change rate; or, obtain a difference value between the fingerprint signal intensity and the image background intensity, and determine a ratio of the difference value to the image background intensity to be the fingerprint signal change rate.

The specific principles and implementations of the system for measuring the finger moisture provided by the embodiment are similar to the embodiments illustrated by FIG. 2 and will not be repeated here.

In the present embodiment, the fingerprint signal change rate can be obtained in different manners, which ensures the accuracy and the reliability of the fingerprint signal change rate in various implementations, and improves the conveniences and reliability for user; then the fingerprint signal change rate is compared with the predefined different change rate thresholds, so that the finger moisture can be determined accurately, thus the accuracy and reliability of the use of the system for measuring the finger moisture is ensured.

On the basis of the above-mentioned embodiments and with reference to FIG. 13, when the processor 100 obtains the fingerprint signal intensity according to the fingerprint image, in a possible implementation, the processor 100 can be configured to: obtain a mean value of ridge signal intensities corresponding to ridges of the finger and a mean value of valley signal intensities corresponding to valleys of the finger in the fingerprint image; determine a difference value between the mean value of the ridge signal intensities and the mean value of the valley signal intensities to be the fingerprint signal intensity.

In another possible implementation, the processor 100 can be configured to: obtain a maximum signal intensity and a minimum signal intensity of pixels in a desired region in the fingerprint image; determine the fingerprint signal intensity according to the maximum signal intensity and the minimum signal intensity.

When the processor 100 obtains the maximum signal intensity and the minimum signal intensity of the pixels in the desired region in the fingerprint image, in a possible implementation, the processor 100 can be configured to: obtain a desired region in the fingerprint image; calculate the signal intensities of all the pixels in the desired region; determine the maximum signal intensity and the minimum signal intensity among the signal intensities.

In another possible implementation, the processor 100 can be configured to: obtain a neighborhood corresponding to each pixel in the fingerprint image; calculate a maximum signal intensity and a minimum signal intensity of pixels in the neighborhood to obtain the maximum signal intensity and the minimum signal intensity corresponding to each pixel; obtain the desired region in the fingerprint image; determine the maximum value among the maximum signal intensities corresponding to all the pixels in the desired region to be the maximum signal intensity of the pixels in the desired region; determine the minimum value among the minimum signal intensities corresponding to all the pixels in the desired region to be the minimum signal intensity of the pixels in the desired region.

Moreover, when the processor 100 determines the fingerprint signal intensity according to the maximum signal intensity and the minimum signal intensity, the processor 100 can be configured to: determine a difference value between the maximum signal intensity and the minimum signal intensity to be the fingerprint signal intensity; or, obtain a signal intensity difference value between the maximum signal intensity and the minimum signal intensity corresponding to each pixel; in the desired region, average out the sum of signal intensity difference values of all the pixels over all the pixels in the desired region to obtain a signal intensity mean value; determine the signal intensity mean value to be the fingerprint signal intensity.

The specific principles and implementations of the system for measuring the finger moisture provided by the embodiment are similar to the embodiments illustrated by FIGS. 3-8 and will not be repeated here.

On the basis of the above-mentioned embodiments and with reference to FIG. 13, in specific applications, in order to further ensure the accuracy and reliability of the system for measuring finger moisture, the system provided by the present embodiment can also include: a pressure sensor 300 communicatively connected with the processor 100;

the pressure sensor 300 is configured to obtain information of a pressure applied by the finger while obtaining the fingerprint image;

the processor 100 is further configured to: if the information of the pressure is greater than or equal to the predefined pressure threshold, obtain the fingerprint signal intensity and the image background intensity according to the fingerprint image; or, if the information of the pressure is smaller than the predefined pressure threshold, stop obtaining the fingerprint signal intensity and the image background intensity.

The specific principles and implementations of the system for measuring the finger moisture provided by the embodiment are similar to the embodiments illustrated by FIG. 9 and will not be repeated here.

In the present embodiment, the pressure sensor 300 obtains the information of pressure applied by the finger while obtaining the fingerprint image, and the processor 100 is used to analyze the information of the pressure, so that the definition of the fingerprint image can be determined to control a further operation of the measuring system. Specifically, when the fingerprint image is relatively clear, the fingerprint signal intensity and the image background intensity can be obtained directly; when the fingerprint image is relatively fuzzy, the obtaining of the fingerprint signal intensity and the image background intensity is stopped, which further improves the accuracy of the measuring system.

On the basis of the above-mentioned embodiments and with reference to FIG. 13, in order to further improve the practicability of the measuring system, the measuring system of the present embodiment can include: the memory 400 communicatively connected with the processor 100;

the memory 400 is configured to store data of finger moisture in the predefined database;

the processor 100 is further configured to determine the user's health condition according to the data of finger moisture of each user stored in the database.

The processor 100 is further configured to: identify the user according to the fingerprint image before storing the data of finger moisture in the predefined database; if the user is successfully identified, then store the data of finger moisture in the predefined database; or, if the user fails to be identified, then prompt for the failure in user identifying.

It should be noted that, the above-mentioned memory 400 is further configured to store the program instructions corresponding to the method for measuring finger moisture. And the processor 100 can execute the above-mentioned program instructions to implement the corresponding function of measuring the finger moisture; moreover, the specific principles and implementations of the system for measuring the finger moisture provided by the present embodiment are similar to the embodiments illustrated by FIGS. 10-11 and will not be repeated here.

In the present embodiment, the processor 100 identifies the user's identity, if the verification of the user's identity is passed, the memory 400 is used to store the data of finger moisture in the corresponding storing area in the database, which facilitates determining the user's health condition according to the data of finger moisture of each user stored in the database, ensures the practicability of the measuring system, and also improves the convenience and reliability of the measuring system.

The technical solutions and technical features of the various embodiments mentioned above can be used alone or in combination without conflicting with the present invention, which are to be construed as belonging to equivalent embodiments within the scope of the present application as long as not going beyond the scope of knowledge of those skilled in the art.

In several embodiments provided by the present invention, it should be understood that the disclosed related apparatuses and methods may be implemented in other ways. For example, the embodiments of the apparatus described above are merely illustrative, for example, the division of the modules or units is only a division of logical functions, and there may be other forms of division in actual implementations; for example, multiple units and components may be combined or integrated into another system, or some features may be ignored or not implemented. In addition, the coupling or direct coupling or communication connection shown or discussed may be indirect coupling or communication connection through a number of interfaces, devices or units and may be electrical, mechanical, or otherwise.

The units described as the separate components may be or may not be physically separated, and the components shown as units may be or may not be physical units, that is to say, they may be located in one place or may be distributed over a plurality of network elements. The part or all of the units may be selected according to the actual needs to achieve the object of the present embodiment solutions.

In addition, the functional units in the various embodiments of the present invention may be integrated in one processing unit; or each unit may be physically separate to each other; or two or more units may be integrated in one unit. The above-mentioned integrated unit can be implemented either in a form of hardware or in a form of a software functional unit.

The integrated unit may be stored in a computer-readable storage medium if it is implemented in the form of a software functional unit and sold or used as an independent product. Based on this understanding, the technical solutions of the present invention essentially, or the parts that contribute to the prior art, or parts or all of the technical solutions may be embodied in the form of a software product stored in a storage medium, the software product including a number of instructions for causing the computer processor to perform all or part of the steps of the methods described in the various embodiments of the present invention. The aforementioned storage medium includes a variety of mediums such as a USB disk, a mobile hard disk, a read-only memory (ROM), a random access memory (RAM), a magnetic disk, an optical disk or other medium on which program codes can be stored.

The foregoing contents are merely embodiments of the present invention and are not intended to limit the scope of the invention. Any transformation of equivalent structure or equivalent process made by means of the description and drawings of the invention, or any direct or indirect application in other related fields is included in the scope of the present invention.

Finally, it should be noted that the above embodiments are merely illustrative of the technical solutions of the present invention and are not intended to limit the same. Although the present invention has been described in detail with reference to the foregoing embodiments, it will be understood by those of ordinary skill in the art that it is still possible to modify the technical solutions described in the foregoing embodiments or to equivalently substitute some or all of the technical features therein, and these modifications or substitutions do not make the essence of the corresponding technical solutions depart from the scope of embodiments of the present invention.

What is claimed is:

1. A method for measuring finger moisture, comprising:
   obtaining a fingerprint image;
   obtaining a fingerprint signal intensity and an image background intensity according to the fingerprint image;
   determining the finger moisture according to the fingerprint signal intensity and the image background intensity identifying a user according to the fingerprint image; if the user is successfully identified, storing data of the finger moisture in a predefined database and determining a health condition of each user according to the data of the finger moisture of the user stored in the predefined database.

2. The method according to claim 1, wherein the obtaining the fingerprint signal intensity according to the fingerprint image comprises:
obtaining a mean value of ridge signal intensities corresponding to ridges of a finger in the fingerprint image, and a mean value of valley signal intensities corresponding to valleys thereof;
determining a difference value between the mean value of the ridge signal intensities and the mean value of the valley signal intensities to be the fingerprint signal intensity.

3. The method according to claim 1, further comprising:
obtaining information of a pressure applied by a finger while obtaining the fingerprint image;
if the information of the pressure is greater than or equal to a predefined pressure threshold, obtaining the fingerprint signal intensity and the image background intensity according to the fingerprint image; or
if the information of the pressure is smaller than the predefined pressure threshold, stopping obtaining the fingerprint signal intensity and the image background intensity.

4. The method according to claim 1, wherein the determining the finger moisture according to the fingerprint signal intensity and the image background intensity comprises:
obtaining a fingerprint signal change rate according to the fingerprint signal intensity and the image background intensity;
if the fingerprint signal change rate is greater than or equal to a predefined first change rate threshold, determining that the finger moisture is overly wet; or
if the fingerprint signal change rate is less than the predefined first change rate threshold and greater than or equal to a predefined second change rate threshold, determining that the finger moisture is moderate; or
if the fingerprint signal change rate is less than the predefined second change rate threshold, determining that the finger moisture is overly dry.

5. The method according to claim 4, wherein the obtaining the fingerprint signal change rate according to the fingerprint signal intensity and the image background intensity comprises:
determining a ratio of the fingerprint signal intensity to the image background intensity to be the fingerprint signal change rate; or
obtaining a difference value between the fingerprint signal intensity and the image background intensity, and determining a ratio of the difference value to the image background intensity to be the fingerprint signal change rate.

6. The method according to claim 1, wherein the obtaining the fingerprint signal intensity according to the fingerprint image comprises:
obtaining a maximum signal intensity and a minimum signal intensity of pixels within a desired region in the fingerprint image;
determining the fingerprint signal intensity according to the maximum signal intensity and the minimum signal intensity.

7. The method according to claim 6, wherein the obtaining the maximum signal intensity and the minimum signal intensity of pixels within the desired region in the fingerprint image comprises:
obtaining the desired region in the fingerprint image;
calculating signal intensities of all pixels in the desired region;
determining the maximum signal intensity and the minimum signal intensity among the signal intensities.

8. The method according to claim 6, wherein the obtaining the maximum signal intensity and the minimum signal intensity of pixels within the desired region in the fingerprint image comprises:
obtaining a neighborhood corresponding to each pixel in the fingerprint image;
calculating a maximum signal intensity and a minimum signal intensity of pixels in the neighborhood for each pixel, and obtaining the maximum signal intensity and the minimum signal intensity corresponding to the each pixel;
obtaining the desired region in the fingerprint image;
determining a maximum value among maximum signal intensities corresponding to all pixels in the desired region to be the maximum signal intensity of the pixels in the desired region; determining a minimum value among minimum signal intensities corresponding to all the pixels in the desired region to be the minimum signal intensity of the pixels in the desired region.

9. The method according to claim 8, wherein the determining the fingerprint signal intensity according to the maximum signal intensity and the minimum signal intensity comprises:
determining a difference value between the maximum signal intensity and the minimum signal intensity to be the fingerprint signal intensity; or
obtaining a signal intensity difference value between the maximum signal intensity and the minimum signal intensity corresponding to each pixel; averaging out a sum of signal intensity difference values of all pixels in the desired region in the desired region to obtain a signal intensity mean value; determining the signal intensity mean value to be the fingerprint signal intensity.

10. An apparatus for measuring finger moisture, comprising a processor and a memory storing instructions thereon, the processor when executing the instructions, being configured to:
obtain a fingerprint image;
obtain a fingerprint signal intensity and an image background intensity according to the fingerprint image,
determine the finger moisture according to the fingerprint signal intensity and the image background intensity, identify a user according to the fingerprint image; if the user is successfully identified, store data of the finger moisture in a predefined database and determine a health condition of each user according to the data of the finger moisture of the user stored in the predefined database.

11. The apparatus according to claim 10, wherein the processor is further configured to:
obtain a mean value of ridge signal intensities corresponding to ridges of a finger in the fingerprint image, and a mean value of valley signal intensities corresponding to valleys thereof;
determine a difference value between the mean value of the ridge signal intensities and the mean value of the valley signal intensities to be the fingerprint signal intensity.

12. The apparatus according to claim 10, wherein the processor is further configured to:
   obtain a fingerprint signal change rate according to the fingerprint signal intensity and the image background intensity;
   if the fingerprint signal change rate is greater than or equal to a predefined first change rate threshold, determine that the finger moisture is overly wet; or
   if the fingerprint signal change rate is less than the predefined first change rate threshold and greater than or equal to a predefined second change rate threshold, determine that the finger moisture is moderate; or
   if the fingerprint signal change rate is less than the predefined second change rate threshold, determine that the finger moisture is overly dry.

13. The apparatus according to claim 12, wherein the processor is further configured to:
   determine a ratio of the fingerprint signal intensity to the image background intensity to be the fingerprint signal change rate; or
   obtain a difference value between the fingerprint signal intensity and the image background intensity, determine a ratio of the difference value to the image background intensity to be the fingerprint signal change rate.

14. The apparatus according to claim 10, wherein the processor is further configured to:
   obtain a maximum signal intensity and a minimum signal intensity of pixels within a desired region in the fingerprint image;
   determine the fingerprint signal intensity according to the maximum signal intensity and the minimum signal intensity.

15. The apparatus according to claim 14, wherein the processor is further configured to:
   obtain the desired region in the fingerprint image;
   calculate signal intensities of all pixels in the desired region;
   determine the maximum signal intensity and the minimum signal intensity among the signal intensities.

16. The apparatus according to claim 14, wherein the processor is further configured to:
   obtain a neighborhood corresponding to each pixel in the fingerprint image;
   calculate a maximum signal intensity and a minimum signal intensity of pixels in the neighborhood for each pixel, and obtain the maximum signal intensity and the minimum signal intensity corresponding to the each pixel;
   obtain the desired region in the fingerprint image;
   determine a maximum value among maximum signal intensities corresponding to all pixels in the desired region to be the maximum signal intensity of the pixels in the desired region; determine a minimum value among minimum signal intensities corresponding to all the pixels in the desired region to be the minimum signal intensity of the pixels in the desired region.

17. The apparatus according to claim 16, wherein the processor is further configured to:
   determine a difference value between the maximum signal intensity and the minimum signal intensity to be the fingerprint signal intensity; or
   obtain a signal intensity difference value between the maximum signal intensity and the minimum signal intensity corresponding to each pixel;
   average out a sum of signal intensity difference values of all pixels in the desired region over in the desired region to obtain a signal intensity mean value;
   determine the signal intensity mean value to be the fingerprint signal intensity.

18. A system for measuring finger moisture, comprising: an optical imaging collector, a processor communicatively connected with the optical imaging collector and a memory;
   the optical imaging collector is configured to: collect a fingerprint image, and send the collected fingerprint image to the processor;
   the processor is configured to: obtain the fingerprint image; obtain a fingerprint signal intensity and an image background intensity according to the fingerprint image; determine the finger moisture according to the fingerprint signal intensity and the image background intensity; identify a user according to the fingerprint image; if the user is successfully identified, determine a health condition of each user according to data of the finger moisture before the data of the finger moisture of the user is stored in a predefined database; the memory is configured to: store the data of the finger moisture in the predefined database.

* * * * *